United States Patent [19]
Kahne et al.

[11] Patent Number: 5,571,795
[45] Date of Patent: Nov. 5, 1996

[54] DERIVATIVE-COMPOUND-CONJUGATES AND PHARMACEUTICAL COMPOSITIONS COMPRISING SAME

[75] Inventors: Daniel E. Kahne; Suzanne Walker Kahne, both of Princeton, N.J.

[73] Assignee: The Trustees of Princeton University, Princeton, N.J.

[21] Appl. No.: 989,667

[22] Filed: Dec. 14, 1992

Related U.S. Application Data

[63] Continuation-in-part of Ser. No. 806,985, Dec. 13, 1991.
[51] Int. Cl.$^6$ .................. A61K 31/70; A61K 31/56; C07J 17/00; C07J 41/00
[52] U.S. Cl. .................. 514/26; 514/178; 514/182; 536/5; 540/106
[58] Field of Search .................. 71/806, 985; 514/26, 514/178, 182; 536/5; 540/106

[56] References Cited

U.S. PATENT DOCUMENTS

| | | |
|---|---|---|
| 3,036,061 | 5/1962 | MacPhillamy . |
| 4,150,114 | 4/1979 | Smith . |
| 4,260,736 | 4/1981 | Asano et al. . |
| 4,360,663 | 11/1982 | Asano et al. . |
| 4,900,555 | 2/1990 | Cheng et al. . |
| 4,902,505 | 2/1990 | Pardridge et al. . |
| 4,959,358 | 9/1990 | Carey et al. . |
| 5,116,817 | 5/1992 | Anik . |
| 5,144,017 | 9/1992 | LaBella et al. . |
| 5,338,837 | 8/1994 | Kahne .................. 536/5 |

FOREIGN PATENT DOCUMENTS

| | | |
|---|---|---|
| 0101659 | 6/1983 | European Pat. Off. . |
| 0417725 | 3/1991 | European Pat. Off. . |
| 2007410 | 1/1970 | France . |
| 1527605 | 10/1978 | United Kingdom . |

OTHER PUBLICATIONS

Kahne, Daniel et al. *JACS*, 111: 6881–82, (1989).
Oehlke et al. *Pharmazie* 34: 383–386, (1979).
Riccio et al. *J. Org. Chem* 51(4): 533–536, (1986).
Chemical Abstracts, vol. 92, 1980, No. 59167n, "CMT–Selectin Syntheses. Preparation of Deoxycholic Acid Glucuronides", p. 714, J. Oehlke.
Chemical Abstracts, vol. 115, 1991, No. 72019d, Werner Kramer, et al., "Bile Acid Derivatives, A Process for Their Production and Their Use as Medicines", p. 842.
Chemical Abstract No. 98644b, vol. 94, 1981, J. Oehlke, "Interactions Between Deoxycholic Acid Glucuronides and Glucuronidase".
J. Am. Chem. Soc., vol. 111, No. 17, 1989, Daniel Kahne, et al., "Glycosylation of Unreactive Substrates", pp. 6881–6882.
Proc. Natl. Acad. Sci. USA, vol. 86, pp. 6553–6556, Sep. 1989, Robert L. Letsinger, et al., "Cholesteryl–Conjugated Oligonucleotides: Synthesis, Properties, and Activity as Inhibitors of Replication of Human Immunodeficiency Virus in Cell Culture".

Tetrahedron Letters, vol. 29, No. 38, pp. 4873–4876, 1988, Dearg S. Brown, et al., "Preparation of Cyclic Ether Acetals from 2–Benzenesulphonyl Derivatives: A New Mild Glycosidation Procedure".
Carbohydrate Research, vol. 177, 1988, pp. c13–c17, Falguni Dasgupta, et al., "Alkyl Sulfenyl Triflate as Activator in the Thioglycoside–Mediated Formation of Beta–Glycosidic Linkages During Oligosaccharide Synthesis".
"Benzeneselenenyl Triflate as a Promoter of Thioglycosides: A New Method for O–Glycosylation Using Thioglycosides)", Yukishige Ito, et al., pp. 1061–1064.
"Synthesis of 1,2–CIS–Linked Glycosides Using Dimethyl-(Methylthio)Sulfonium Triflate as Promoter and Thioglycosides as Glycosyl Donors", Fredrik Andersson, et al., pp. 3919–3922.
Carbohydrate Research, vol. 139, 1985, pp. 105–113, Hans Lonn, "Synthesis of a Tri– and a Hepta–Saccharide Which Contain Alpha–L–Fucopyranosyl Groups and are Part of the Complex Type of Carbohydrate Moiety of Glycoproteins".
Carbohydrate Research, vol. 116, 1983, pp. 162–165, J. Garegg, et al., "A Reinvestigation of Glycosidation Reactions Using 1–Thioglycosides as Glycosyl Donors and Thiophilic Cations as Promoters".
J. Am. Chem. Soc., vol. 105, No. 8, 1983, pp. 2430–2434, K. C. Nicolaou, et al., "A Mild and General Method for the Synthesis of O–Glycosides".
"A Potentially Versatile Synthesis of Glycosides", R. J. Ferrier, et al., vol. 27, 1973, pp. 55–61.
J. Org. Chem., vol. 51, No. 4, 1986, Raffaele Riccio, et al., pp. 533–536, "Two New Steroidal Glycoside Sulfates, Longicaudoside–A and –B, from the Mediterranean Ophiuroid Ophioderma Longicaudum".
Mitt.: Hoppe–Seyler's Z. physiol. Chem. 359, 803 (1978), J. Oehlke, pp. 383–386, "Darstellung Von Desoxycholsaureglucuroniden".
The Journal of Biological Chemistry, vol. 267, No. 26, 1992, pp. 18598–18604, Werner Kramer, et al., "Liver–Specific Drug Targeting by Coupling to Bile Acids".
Proc. Natl. Acad. Sci. USA, vol. 82, pp. 7419–7423, Nov. 1985, G. S. Gordon, et al., "Nasal Absorption of Insulin: Enhancement by Hydrophobic Bile Salts".
J. Am. Chem. Soc. 1992, vol. 114, pp. 7319–7320, Yuan Cheng, et al., "Facial Amphiphiles".
Neurosurgery, vol. 12, No. 6, Jun. 1983, pp. 606–612, Melvin K. Spigelman, et al., "Intracarotid Dehydrocholate Infusion: A New Method for Prolonged Reversible Blood-–Brain Barrier Disruption".
Proc. Natl. Acad. Sci. USA, vol. 78, No. 9, pp. 5908–5912, Sep. 1981, D. H. Malinowska, et al., "Properties of the Gastric Proton Pump in Unstimulated Permeable Gastric Glands".

*Primary Examiner*—John Kight
*Assistant Examiner*—Howard C. Lee
*Attorney, Agent, or Firm*—Lowe, Price, LeBlanc & Becker

[57] ABSTRACT

Novel glycosylated steroid derivatives for facilitating the transport of compounds across biological membranes, either in admixture or as conjugates, are disclosed. A novel process for efficient synthesis of these glycosylated steroid derivatives, using activated glycosyl sulfoxide intermediates is also provided.

68 Claims, 3 Drawing Sheets

DERIVATIVE-COMPOUND-CONJUGATES AND PHARMACEUTICAL COMPOSITIONS COMPRISING SAME

This invention was made with Government support under Grant No. N0014-91-J-1230, awarded by Office of Naval Research. The Government has certain rights in this invention.

This application is a continuation-in-part of application Ser. No. 07/806,985, filed Dec. 13, 1991, the disclosure of which is hereby incorporated by reference.

BACKGROUND OF THE INVENTION

The present invention is generally directed to novel glycosylated steroid derivatives for facilitating the transport of molecules across biological membranes and the blood-brain barrier. The invention is further directed to a novel glycosylation process for the efficient synthesis of these glycosylated steroid derivatives. To elicit the desired biological response, a molecule of diagnostic, prophylactic, or therapeutic interest [termed herein "therapeutically-significant molecule" or "therapeutically-significant-compound"] must be available in an effective concentration at its site of action. Many factors determine the concentration of a therapeutically-significant-compound that ultimately reaches the site of action, including the amount administered, and the extent and rate of the compound's absorption, distribution, biotransformation, and excretion. [Goodman and Gilman, *The Pharmacological Basis of Therapeutics,* 6th Edition, MacMillan Publishing Co., Inc., New York, 1980, pp. 1–39]. The foregoing factors may, in turn, be influenced by the route chosen for administration of the therapeutically-significant-compound.

The most common routes of administration of therapeutically-significant-compounds are parenteral (intravenous, subcutaneous, and intramuscular) and enteral (oral ingestion), although methods to administer therapeutically-significant-compounds across the skin or mucosa (oral, nasal, rectal, vaginal, etc.) also are known. Parenteral methods are considered to be extremely effective in general, allowing for rapid increases in blood levels of a wide range of therapeutically-significant-compounds. Parenteral methods are advantageous in that they circumvent first-passage hepatic metabolism. However, parenteral administration of a therapeutically-significant-compound can cause pain, irritation, possible tissue damage over the long term, and carries a potential risk of infection. In addition, parenteral methods frequently are inconvenient, particularly those that are restricted to trained medical personnel (e.g., intravenous methods).

Enteral methods are more convenient than parenteral methods, and generally are more economical and acceptable to the recipients. However, orally administered, therapeutically-significant-compounds may be inefficiently absorbed and the time from ingestion to absorption may prohibit effective use in emergency situations. Moreover, many therapeutically-significant-compounds cannot be orally administered as they are destroyed, prior to reaching their site of action, by the digestive enzymes, acid, and surface-active lipids in the gut. Other therapeutically-significant-compounds are subject to extensive, first-passage hepatic metabolism, rendering them ineffective following oral administration.

Non-parenteral methods which circumvent problems associated with instability of drug preparations in the gut and first-passage hepatic metabolism long have been sought. Administration via transdermal, oral mucosal, rectal, and nasal routes are among the alternatives which have been explored. Such alternatives further include administering the therapeutically-significant-compound orally, but encapsulated in a protective delivery system designed to extrude the contents at a predetermined point in the lower gastrointestinal tract. However, the efficacy of these alternative drug delivery methods often is limited by poor absorption of the therapeutically-significant-compounds at the site of delivery or application. Effective strategies to enhance absorption of therapeutically-significant-molecules across cell membranes could enhance the efficacy of many known drug preparations which are poorly absorbed regardless of the method of administration. Such strategies to enhance transmembrane absorption could be particularly useful for therapeutically-significant-compounds that are administered across the skin and mucosal tissues, including mucosal tissues of the gastrointestinal, genitourinary, and respiratory tracts.

The basic structural unit of biological membranes is a phospholipid bilayer, in which are embedded proteins of various size and composition. The surfaces of the phospholipid bilayer, which project into the aqueous cellular environment, are formed by the hydrophilic heads of the phospholipids; the interior, by the fatty acyl hydrophobic tails. The membrane proteins may be involved in transport processes and also may serve as receptors in cellular regulatory mechanisms.

Natural mechanisms for traversal of biological membranes include passive diffusion, facilitated diffusion, active transport, receptor-mediated endocytosis and pinocytosis. Passive diffusion works best for small molecules which are lipid-soluble. However, biological membranes are essentially impermeable to most water-soluble molecules, such as nucleosides, amino acids, proteins, and other hydrophilic, therapeutically-significant-molecules. Such molecules enter cells via some type of carrier-mediated transport system in which specific entities facilitate traversal of the membrane. Natural carriers for facilitating traversal of the membrane are of limited utility, however, as such carriers will accept substrates of only a predetermined molecular configuration. Many therapeutically-significant-compounds are not efficiently absorbed because they are neither lipophilic enough to cross cell membranes by passive diffusion nor recognized by the natural transport systems.

Strategies to enhance the uptake of therapeutically-significant-molecules across biological membranes have been investigated previously and fall into two broad categories. The first category includes all strategies in which the structure of the therapeutically-significant-compound is changed, either by making the compound more lipophilic itself, or by conjugating the compound to other entities known to interact with phospholipid membranes. The common goal of these strategies has been to increase passive diffusion across the membrane by lowering the energy barrier to diffusion and/or by increasing the local concentration of the compound at the membrane surface. Also included in the first category is a strategy for conjugating the therapeutically-significant-compound to entities known to interact with transport machinery embedded in the biological membranes, the goal being to take advantage of the transport machinery (either active or facilitated transport or receptor-mediated endocytosis) to increase delivery of the compound across the membrane.

Many investigators are studying the feasibility of increasing the efficacy of hydrophilic compounds by conjugating these compounds to entities known to interact with phospholipid membranes. Among the techniques reported are utilization of oligonucleotide-cholesterol conjugates

[Letsinger RL et al. "Cholesteryl-conjugated oligonucleotides: Synthesis, properties, and activity as inhibitors of replication of human immunodeficiency virus in cell culture." *Proc. Natl. Acad. Sci.* USA 86: 6553–6556 (September 1989); Stein CA et al. "Mode of Action of 5'-Linked Cholesteryl Phosphorothioate Oligodeoxynucleotides in Inhibiting Syncytia Formation and Infection by HIV-1 and HIV-2 in Vitro." *Biochemistry* 30:2439–2444 (1991)].

Targeting molecules to the brain requires traversal of the blood-brain barrier—a capillary-including system, with unique morphological characteristics, which acts as a system-wide cellular membrane separating the brain interstitial space from the blood. Like biological membranes, the blood-brain barrier is relatively impermeable to many hydrophilic, therapeutically-significant-compounds. Among the strategies which have been developed for targeting compounds to the brain are direct delivery by invasive procedures, intra-arterial infusion of hypertonic substances, and conversion of hydrophilic compounds to lipid-soluble entities. Recent attempts at facilitated transport, as described in U.S. Pat. No. 4,902,505, involve coupling a hydrophilic peptide of interest to a peptide carrier which, by itself, is capable of traversing the barrier via receptor-mediated transcytosis.

The second category of strategies to enhance uptake includes those in which the therapeutically-significant-compounds are administered to specific body surfaces as admixtures with other molecules which are known to permeabilize membranes. For example, several investigators have attempted to mix insulin with adjuvants, such as bile salts, which might enhance nasal insulin absorption. [Hirai et al., *Int. J. Pharmaceutics* 9:165–184 (1981); Hirai et al. *Diabetes* 27: 296–199 (1978); British Patent No. 1,527,506; U.S. Pat. No. 4,153,689; and Pontiroli et al. *Br. Med. J.* 284:303–386 (1982)]. EP 0 444 778 describes the use of alkyl saccharides to enhance the penetration of topically applied drugs across mucus-covered epithelial tissues in general, and the corneal epithelium, in particular. U.S. Pat. No. 4,865,848 to Cheng et al., issued Sep. 12, 1989, discloses the use of sucrose esters, particularly sucrose monolaurate, for enhancing the transdermal flux of transdermally-delivered drugs. U.S. Pat. No. 4,746,508 to Carey et al, issued May 24, 1988, reports the use of fusidic acid and cephalosporin derivatives to increase the permeability of human and animal body surfaces to drugs.

The glycosylated steroid derivatives of the present invention are known to interact with phospholipid membranes, thereby enhancing the penetration of therapeutically-significant-compounds through such membranes, including biological membranes. Like some of the previously used adjuvants and enhancers (e.g., cholic acid and fusidic acid derivatives) the novel derivatives of the present invention are amphiphilic in a facial sense. However, the novel steroid derivatives of the present invention have significantly different structures in that they are glycosylated on their hydrophilic surfaces, a feature not shared by any of the previously-known, facially-amphiphilic steroids. The present inventors have discovered that glycosylation on the hydrophilic surfaces significantly changes both the solubility properties of the steroids and the manner in which they associate. Many of these glycosylated steroids have been shown by the inventors to be more effective that the parent, non-glycosylated, steroids, in permeabilizing both artificial and biological membranes. The novel glycosylated steroid derivatives of the present invention, therefore, may be used to increase the delivery of therapeutically-significant-compounds across cell membranes, either in admixture with the compounds or as conjugates to the compounds.

Prior to the present invention, no method existed for synthesizing all of the glycosylated steroid derivatives of the present invention. Many glycosylation reactions using thioglycosides have been reported. [Ferrier RJ et al. "A Potentially Versatile Synthesis of Glycosides." *Carbohydrate Research* 27: 55–61 (1973); Garegg PJ et al. "A reinvestigation of glycosidation reactions using 1-thioglycosides as glycosyl donors and thiophilic cations as promoters" *Carbohydrate Research* 116: 162–5 (1983); Nicolaou KC et al. "A Mild and General Method for the Synthesis of O-Glycosides." *J Am Chem Soc* 05:2430–2434 (1983); Lonn H. "Synthesis of a tri- and a hepta-saccharide which contain α-L-fucopyranosyl groups and are part of the complex type of carbohydrate moiety of glycoproteins."*Carbohydrate Research* 39:105–113 (1985); Andersson F et al. "Synthesis of 1,2-cis-linked glycosides using dimethyl(methylthio)sulfonium triflate as promoter and thioglycosides as glycosyl donors." *Tetrahedron Letters* pp. 3919–3922 (1986); Brown DS et al. "Preparation of cyclic ether acetals from 2-benzenesulphonyl derivatives: a new mild glycosidation procedure." *Tetrahedron Letters* 29/38: 4873–4876 (1988); Ito Yet al. "Benzeneselenenyl triflate as a promoter of thioglycosides: a new method for O-glycosylation using thioglycosides." *Tetrahedron Letters* pp. 1061–4 (1988); Dasgupta F. et al. "Alkyl sulfonyl triflate as activator in the thioglycoside-mediated formation of β-glycosidic linkages during oligosaccharide synthesis." Carbohydrate Research 177: c13–c17 (1988)]. However, none of these reported methods teach the use of a glycosyl sulfoxide as a glycosylating agent.

Utilization of an activated glycosyl sulfoxide intermediate in a process for glycosylating steroids, previously has been reported by the inventors in *J. Am. Chem. Soc.* 111:6881–2 (1989), the content of which is hereby incorporated by reference. However, the reported method represents only preliminary results on the glycosylation of steroids of the Formula (I). More specifically, further experimentation in the series has revealed unique reaction conditions which are necessary to achieve the efficient and stereo-selective synthesis of glycosylated compounds of the Formula (I). The reaction solvent used plays a critical role in the stereoselectivity of glycosylation. Using a nonpolar, aprotic solvent increases selectivity for alpha (α) glycosidic bond formation while the use of a polar, aprotic solvent such as propionitrile increases selectivity for beta (β) glycosidic bond formation. The type of sulfoxide used in the glycosylation reaction also affects the outcome of the reaction. For example, it is vital to use the para-methoxy phenyl sulfoxide as the leaving group in the novel process described herein to obtain good yields of beta (β) selectivity in the glycosidic bond formation. The yield of the glycosylation reaction yielding alpha (α) or beta (β) glycosidic linkages also may be increased by the use of less than one equivalent of triflic anhydride in the glycosylation process.

Finally, the protecting groups on the glycosyl donor also have an impact on the stereochemical course of the glycosylation reaction. When the protecting group used on the glycosyl donor is pivaloyl, only beta (β) glycosidic bonds are formed in the glycosylation process, regardless of whether an aprotic, non-polar solvent or an aprotic, polar solvent is used for the reaction. The above factors taken together indicate that one skilled in the art could not have practiced the invention without the detailed further experimentation provided herein.

SUMMARY OF THE INVENTION

The present invention is generally directed to, novel, facially-amphiphilic, glycosylated steroid derivatives which have been found to be soluble in both aqueous and membrane-like environments. These unique solubility properties permit the glycosylated steroid derivatives to facilitate the transport of other molecules across biological membranes and the blood brain barrier. It is, therefore, contemplated that the glycosylated steroid derivatives of the present invention can be used, either in admixture with the therapeutically-significant-molecules or by being conjugated to such molecules, to enhance delivery of the molecules across body surfaces including, but not limited to, the buccal, sublingual, conjunctival, rectal, gastric, intestinal, endometrial, cervical, vaginal, or colonic epithelium; the oropharynx, ear canal, respiratory tract, nasopharynx, urethra, urinary bladder, and tympanic membrane. Alternatively, the glycosylated steroid derivatives of the present invention may be administered in admixture with the glycosylated steroid derivative/therapeutically-significant-molecule conjugate [hereinafter referred to as the "derivative-compound-conjugate"] to further enhance facilitation of trans-surface and trans-membrane transport.

It is further contemplated that the novel glycosylated steroids of the present invention may be used for the delivery of antiviral agents, systemic insecticides, and herbicides, across plant surfaces; and, for the delivery of contact insecticides and miticides, across arthropod surfaces.

A novel process for obtaining these novel, facially-amphiphilic, glycosylated steroid derivatives and other glycosylated steroids is also disclosed.

Of particular interest are the steroid derivatives of the general formula (I)

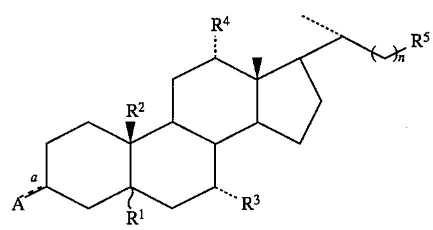

(I)

wherein

A is O, OH, $OR^6$, $NR^7R^8$, $N_3$, $NHCOR^7$, OCOAr $O-\overset{\overset{O}{\|}}{C}-OR^9$, $OCOR^9$, $NHCH_2C_6H_5$;

Ar is phenyl or phenyl substituted with 1–3 groups selected from the group consisting of halogen, $C_1$–$C_{12}$ alkyl of $C_1$–$C_3$ alkoxy;

a is a single bond in the alpha or beta configuration with the proviso that when A=O, a is a double bond;

$R^1$ is H which is cis or trans to $R^2$;

$R^2$ is $CH_3$;

$R^3$ is H, OH or $OR^6$;

$R^4$ is H, OH or $OR^6$;

$R^5$ is $CO_2R^{10}$, $CH_2OR^9$, $CONH_2$, $CONHR^7$, $CONR^7R^8$, $\overset{\overset{O}{\|}}{C}-S-R^{10}$, $CH_2S(O)_p-S-R_{10}CH_2NH_2$, $CH_2NHR^7$, $CH_2NR^7R^8$, $CH^2-S(O)_p-S-R^{10}$;

$R^6$ is a monosaccharide where the glycosidic linkage at the anomeric carbon atom in said monosaccharide is alpha of beta or is an oligosaccharide of 2–10 monosaccharides where the glycosidic linkage at any of the anomeric carbon atoms in each monosaccharide residue of the oligosaccharide is independently alpha or beta;

$R^7$ and $R^8$, independently are H, $C_1$–$C_4$ alkyl, $C_3$–$C_7$cycloalkyl, $C_4$–$C_{10}$ alkylcycloalkyl, phenyl, benzyl, or, taken together are $(CH_2)_f$, where f=3–6;

$R^9$ is H or, $C_1$–$C_3$ alkyl;

$R^{10}$ is H, $C_1$–$C_{10}$ alkyl, $C_1$–$C_{10}$ alkenyl, $C_1$–$C_{10}$ alkynyl, $C_6H_5$ or $CH_2C_6H_5$;

monosaccharide is a protected or deprotected hexose or deoxyhexose selected from the group consisting of D- or L-allose, D- or L-altrose, D- or L-glucose, D- or L-mannose, D- or L-gulose, D- or L-idose, D- or L-galactose, and D- or L-talose or a protected or deprotected furanose or deoxyfuranose selected from the group consisting of D- or L-ribose, D- or L-arabinose, D- or L-xylose and D- or L-lyxose where said protecting groups for the hydroxy groups of said hexoses or furanoses are selected from the group consisting of benzyl, pivaloyl, trimethylsilyl, tert-butyldimethylsilyl, tert-butyldiphenylsilyl, triisopropylsilyl, acetyl, tetrahydropyranyl, benzoyl, $C_1$–$C_3$ alkyl, isopropylidene, benzylidene, (2-methoxyethoxy)methyl, orthoester, paramethoxybenzyl and allyl;

p is 0, 1 or 2;

n is 0, 1 or 2;

or a pharmaceutically suitable salt thereof.

Of further interest are conjugates of a therapeutically-significant-compound linked to a compound of Formula (I) through any of $R_5$, where said therapeutically-significant-compound includes, but is not limited to, anti-bacterials such as polyene antibiotics (erythromycin), beta-lactam antibiotics, and peptide-based or steroidal antibiotics; anti-fungal agents such as 10-thiastearic acid and 24-thiacholestanol; peptides or proteins, such as regulatory factors, enzymes, antibodies, hormones, and toxins; nucleotides, nucleosides and nucleic acids; and saccharides; and wherein the A and B rings of the steroidal residue of said compounds of Formula (I) may be cis or trans to one another; and the O glycosidic linkage at C-7 and C-12 may be in the alpha or beta configuration, each independently of the other. Also provided are methods for facilitating the transport of any therapeutically-significant-compound across a biological membrane, either in admixture with a glycosylated steroid derivative of the present invention or in the form of a derivative-compound-conjugate. Alternatively, a method is provided for further enhancing trans-membrane transport of the derivative-compound-conjugate by administering the derivative-compound-conjugate in admixture with a glycosylated steroid derivative of the present invention, which may be either the same as, or different from, the derivative of the conjugate.

Also provided are pharmaceutical compositions containing (1) effective amount of a compound of Formula (I) and a suitable pharmaceutical carrier; (2) an effective amount of a compound of Formula (I), an effective amount of a therapeutically-significant compound, and a suitable pharmaceutical carrier; (3) an effective amount of derivative-compound-conjugate and a suitable pharmaceutical carrier; or (4) an effective amount of a compound of Formula (I), an effective amount of derivative-compound-conjugate, and a suitable pharmaceutical carrier.

The invention is further directed to a novel process (Scheme I) for the efficient synthesis of glycosylated steroid derivatives of the Formula (I) which comprise: (a) reacting a protected glycoside, which is prepared by standard methods for conversion of a sugar well known to those of ordinary skill in the art, where the oxygen atoms at all positions of the sugar except the anomeric position are protected with the same or different groups, with (b) an —S—R entity under standard conditions, where R is $C_1$–$C_{10}$ alkyl, pyrimidyl, furyl, thienyl, pyridyl, phenyl or phenyl substituted with 1–3 groups selected from the group comprising halogen, $C_1$–$C_3$ alkyl, $NO_2$, $C_1$–$C_3$ alkoxy, to yield a protected thio-glycoside which is further reacted with (c) meta-chloroperoxybenzoic acid to yield the corresponding sulfoxide derivative and (d) converted to an activated glycosylating agent intermediate using a triflate-containing compound, such as triflic anhydride, methyl triflate or trimethylsilyl triflate and contacting said activated glycosylating agent with (e) asteroid (in which any oxygens which are not to be glycosylated have been protected by standard methods) in the presence of 2,6-di-tert-butyl-4-methylpyridine in toluene, for formation of alpha, alpha glycosidic linkages, or in propionitrile, for the formation of beta, beta glycosidic linkages thereby yielding a protected glycosylated steroid which is then deprotected by removing the protecting groups by (f) standard procedures to yield glycosylated steroids of the Formula (I). The oxygen-protecting groups utilized may be either electron-withdrawing groups such as esters; or electron-donating groups, such as ethers, including alkyl, silyl, phenyl or benzyl ethers. However, if a pivaloyl ester is the protecting group used, the resulting glycosidic linkage that is formed is always β,β regardless of the solvent used for the reaction. The resulting compounds of the invention may be characterized by proton NMR, $C^{13}$-NMR, high resolution mass spectroscopy, X-ray crystallography and thin layer chromatography.

Also provided is a process for synthesis of the novel derivative-compound-conjugates of the present invention.

Preferred for their ability to permeabilize biological membranes are those compounds of Formula (I) where:
A is OH,

$OCOR^9$, $OCOC6H_4$, $OCOC6H_4$—pOMe, $NH_2$;
a is a single bond;
$R^3$ is $OR^6$;
$R^4$ is $OR^6$;
$R^5$ is $CO_2R^{10}CO_2NR^7R^8$;
$R^6$ is a monosaccharide where the glycosidic linkage at the anomeric carbon atom in said monosaccharide is alpha or beta;
$R^{10}$ is H or $C_1$–$C_{10}$ alkyl;
monosaccharide is a protected or deprotected hexose such as D- or L-glucose where the protecting groups are benzyl or pivaloyl.

Preferred for their ability to permeabilize biological membranes are:

(a) 3α-O-benzoyl-trans-5,10-bis-β,β-7,12- glucosyl cholic acid methyl ester;

(b) 3α-hydroxy-cis-5,10-bis-α,α-7,12-glucosyl cholic acid;

(c) 3α-hydroxy-cis-5,10-bis-α,α-7,12-glucosyl cholic acid methyl ester;

(d) 3α-hydroxy-cis-5,10-bis-α,α-7,12-glycosyl 25-tryptophanyl cholic acid;

(e) 3α-ethylcarbonate-cis-5,10-bis-α,α-7,12glucosyl cholic acid methyl ester;

(f) 3α-O-benzoyl-cis-5,10-bis-α,α-7,12-glucosyl cholic acid methyl ester;

(g) 3α-O-p-methoxybenzoyl-cis-5,10-bis-α,α-7,12 glucosyl cholic acid methyl ester;

(h) 3α-O-benzoyl-cis-5,10-bis-α,α-7,12-glucosyl cholic acid methyl ester;

(i) 3α-hydroxy-cis-5,10-bis-β,β-7,12-glucosyl cholic acid;

(j) 3α-O-benzoyl-trans-5,10-bis-α,α-7,12 glucosyl cholic acid methyl ester;

(k) 3α-hydroxy-trans-5,10-bis-β,β-7,12 glucosyl cholic acid.

Particularly preferred is Compound G above, 3α-O-p-methoxybenzoyl-cis-5,10-bis-α,α-7,12-glucosyl cholic acid methyl ester and its acid form, 3α-O-p-methoxybenzoyl-cis-5,10-bis-α,α-7,12-glucosyl cholic acid.

DETAILED DESCRIPTION OF THE INVENTION

Figure 1:
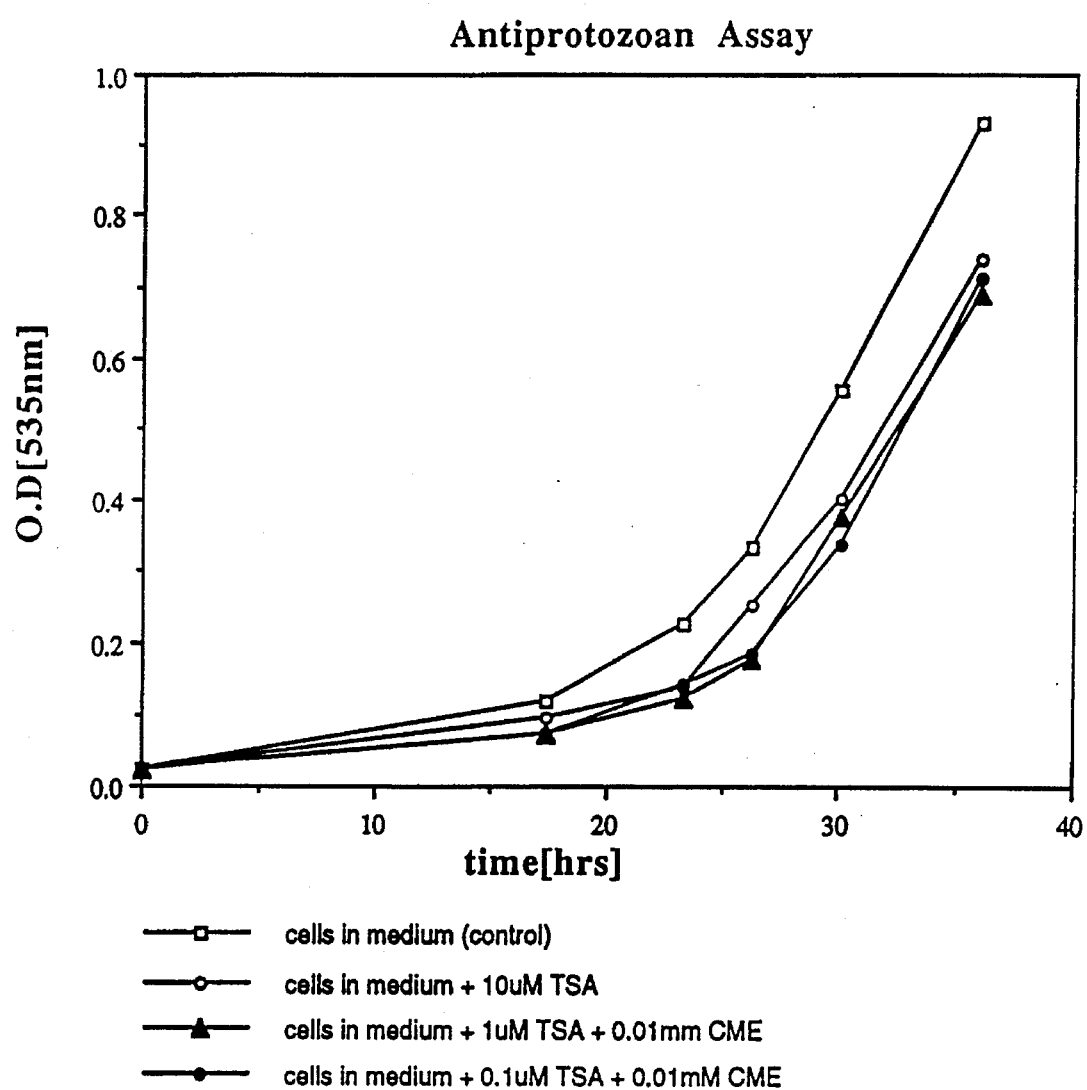
FIG. 1. A graph depicting the enhancing effect of CME, a novel glycosylated steroid derivative of the present invention, on the efficacy of thiastearic acid, an antifungal agent.

The introduction of molecules of diagnostic, prophylactic, or therapeutic interest across body surfaces and/or into cells requires the transversal of one or more semi-permeable biological membranes. The compounds of this invention are useful in permeabilizing biological membranes, thereby assisting body surface and/or membrane transversal of therapeutically-significant-compounds. In one embodiment, the therapeutically-significant-compound is administered in admixture with a glycosylated steroid derivative of the present invention. In another embodiment, trans-surface and/or transmembrane transport is facilitated by administering the therapeutically-significant-compound in the form of a derivative-compound-conjugate in which the compound of interest is conjugated to the glycosylated steroid, i.e., $R^5$ is linked to a therapeutically-significant-compound. Alternatively, the derivative-compound-conjugate may be administered in admixture with a novel glycosylated steroid derivative of the present invention, which may be either the same as, or different from, the derivative of the conjugate.

The novel glycosylated steroid derivatives of the present invention may be expected to enhance the therapeutic efficacy of a wide variety of compounds. As a result, many therapeutic applications for the compounds of the present invention may be contemplated. Membrane permeable therapeutic agents could be used in the treatment of a wide variety of illnesses such as AIDS and other chronic viral infections, cancer, bacterial and fungal infections, and metabolic diseases such as lupus, diabetes and rheumatoid arthritis.

The ability of the novel glycosylated steroid derivatives of the present invention to interact with, and/or permeabilize, biological membranes, is believed to result from the compounds' facial amphiphilicity. The glycosylated surface of the derivatives is hydrophilic; the non-glycosylated surface, hydrophobic. This facially amphiphilic structure confers unusual properties on the molecules, including an ability to self-associate in both hydrophobic and hydrophilic environments, and to organize at amphiphilic interfaces. Some of the glycosylated steroid derivatives of the present invention have now been shown, by the inventors, to crystallize in layers, with alternating hydrophobic and hydrophilic layers.

The non-glycosylated, parent steroid compounds, although possessing some facial amphiphilicity, do not crystallize in register and in organized layers like the glycosylated steroids. In addition, the solubility properties of the glycosylated steroid derivatives of the present invention differ substantially from those of the parent compounds. More particularly, the novel glycosylated steroid derivatives of the present invention, while more soluble than the parent compounds in an aqueous environment are, unexpectedly, not significantly less soluble in an organic environment. Based on these observations, the inventors believe that the novel glycosylated steroid derivatives of the present invention permeabilize membranes by self-associating to form small, reverse micelles, with their hydrophobic surfaces exposed to the lipids within the membranes. These reverse micelles may function as water-filled pores, allowing therapeutically-significant-compounds to pass through, or the presence of these reverse micelles in the membrane may perturb membrane order.

Additionally, the compounds of the present invention facilitate the transport of protons or other ions such as $Ca^{+2}Na^+$, or $K^+$ across biological membranes, indicating their use as potential antifungal or antibiotic agents.

The derivative-compound-conjugate of the present invention can be used in vivo, as a component of a pharmaceutical composition in a manner similar to more conventional therapeutic agents. Administration of the derivative-compound-conjugate to an individual with a chronic viral infection may inactivate the virus or the derivative-compound-conjugate may contain an antisense oligonucleotide sequence which is inhibitory to viral gene or oncogene activity. For the individual with a genetic defect, the therapeutically-significant-compound can be a protein which supplements a missing or defective protein.

The derivative-compound-conjugate may be administered as a pharmaceutical composition via a variety of routes, including subcutaneous, intravenous, intramuscular, intrasternal, intranasal and intracranial injection or infusion. The pharmaceutical composition also may be administered topically or via inhalation.

More specifically, the compounds of this invention, including the compounds of Formula (I) and the derivative-compound-conjugates, can be administered to treat chronic vital infections such as AIDS (Acquired Immune Deficiency Syndrome) or herpes simplex; autoimmune diseases such as lupus, rheumatoid arthritis; diabetes, cystic fibrosis, growth hormone deficiencies; and cancer, by any means that produces contact of the active agents with the appropriate site of action in a mammal. They can be administered by any conventional means available for use in conjunction with pharmaceuticals, either as individual therapeutic agents or in a combination of therapeutic agents. They can be administered alone, but are generally administered with a pharmaceutical carrier selected on the basis of the chosen route of administration and standard pharmaceutical practice.

The dosage administered will, of course, vary depending upon known factors such as the pharmacodynamic characteristics of the particular agent, and its mode and route of administration; age, health, and weight of the recipient; nature and extent of symptoms, kind of concurrent treatment, frequency of treatment, and the effect desired. Usually a daily dosage of therapeutically-significant-compound can be about 0.1 to 100 milligrams per kilogram of body weight. Ordinarily 0.5 to 50, and preferably 1 to 10 milligrams per kilogram per day given in divided doses 1 to 6 times a day or in sustained release form is effective to obtain desired results.

Dosage forms (compositions) suitable for internal administration contain from about 1 milligram to about 500 milligrams of therapeutically-significant-compound per unit. In these pharmaceutical compositions the therapeutically-significant-compound ordinarily will be present in an amount of about 0.5–95% by weight based on the total weight of the composition.

The compositions can be administered orally in solid dosage forms, such as capsules, tablets, and powders, or in liquid dosage forms, such as elixirs, syrups, and suspensions. The compositions also can be administered parenterally, in sterile liquid dosage forms, by inhalation in the form of a nasal spray or lung inhaler, or topically as an ointment, cream or lotion.

Gelatin capsules additionally may contain powdered carriers, such as lactose, sucrose, mannitol, starch, cellulose derivatives, magnesium stearate, stearic acid, and the like. Similar diluents can be used to make compressed tablets. Both tablets and capsules can be manufactured as sustained release products to provide for continuous release of therapeutically-significant-compound over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration additionally may contain suitable stabilizing agents, and if necessary, buffer substances. Antioxidizing agents such as sodium bisulfite, sodium sulfite, or ascorbic acid either alone or combined are suitable stabilizing agents. Also used are citric acid and its salts and sodium EDTA. In addition, parenteral solutions can contain preservatives, such as benzalkonium chloride, methyl or propyl-paraben, and chlorobutanol.

SYNTHESIS

The compounds of Formula (I) can be prepared according to the process shown in Scheme I.

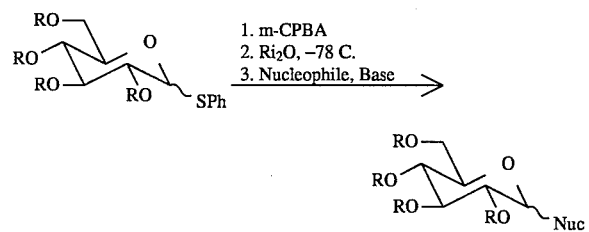

Scheme I

A protected thioglycoside is oxidized with m-chloroperoxybenzoic acid under standard conditions to yield the corresponding sulfoxide. Triflic anhydride (Aldrich) is then added to a solution of the protected glycosyl sulfoxide in toluene at −78° C. followed by the addition of an acid scavenger such as 2,6-di-tert-butyl-4-methyl pyridine (Aldrich Chemical Co.) in toluene and the nucleophile dissolved in toluene at −78° C. After stirring for 15–30 minutes, the reaction was removed from the cold bath and stirred for an additional 10 minutes and quenched by pouring the mixture into aqueous sodium bicarbonate and the protected adduct was isolated by chromatography. Deprotection of the adduct under standard conditions yields compounds of the Formula (I). The appropriate thioglycoside is obtained via standard protection of a selected sugar followed by thioglycoside formation according to methods described above. Via this method, bis-glycosylation of a steroid derivative of the Formula (I) where $R^3$ and $R^4$ are OH selectively produces α,α glycosidic linkages with the glycosyl donor, except where the protecting group used is pivaloyl, in which case only β,β glycosidic linkages are formed regardless of the solvent used for the reaction.

Alternatively, the protected glycosyl sulfoxide, nucleophile and pyridine base are dissolved in propionitrile at −78° C., followed by the addition of triflic anhydride at −78° C. and the product is isolated as described above. Via this method, glycosylation of asteroid derivative of the Formula (I) where $R^3$ and $R^4$ are OH selectively produces β,β glycosidic linkages with the glycosyl donor. It is vital to use the p-methoxy phenyl sulfoxide as the leaving group in the above process to obtain the β,β selectivity in the glycosylation.

The compounds of this invention and their preparation are illustrated further in the following examples. All temperatures are in degrees Centigrade and parts and percentages by weight. In these Examples, unless otherwise indicated, the reactions were performed under an atmosphere of dry argon; "isolation by extraction" refers to the liquid—liquid extraction of a water containing mixture with an indicated solvent, followed by drying the organic phase over sodium sulfate, filtering, and evaporating the solvent under reduced pressure; chromatography refers to the method of medium pressure column chromatography described by W. C. Still, et al., *Journal of Organic Chem.*, 43:2923 (1978).

EXAMPLE 1

Part A:
Perbenzylated-3α-ethylcarbonate-cis-5,10-bis-α,α-glucosyl cholic acid methyl ester.

A 100 ml round bottom flask containing a Teflon® stir bar is flame dried and cooled to −78° C. (acetone/dry ice bath) under argon. 2,3,4,6-tetra-O-benzyl glucose sulfoxide (2.97 g, 4.57 mmol, 4.0 eq.), $C_3$ ethylcarbonate cholic acid (0.563 g, 1.14 mmol, 1.0 eq.) and 2,6-di-tert-butyl-4-methylpyridine (0.936g, 4.57 mmol, 4.0 eq.) are each dried by azeotroping each separately three times with toluene (15.0 ml). Triflic anhydride (824 μl, 4.57 mmol, 4.0 eq.) is added to the glycosyl sulfoxide dissolved in toluene (5.0 ml) at −78° C. To this mixture is then added the pyridine base in toluene (5.0 ml). After five minutes, the cholic acid derivative, dissolved in methylene chloride (1.0 ml) and toluene (5.0 ml). is added. The reaction is allowed to stir at −78° C. for thirty minutes and then removed from the dry ice bath. After ten minutes, the reaction is quenched by the addition of saturated sodium bicarbonate and the product was isolated by extraction with methylene chloride and purified by flash chromatography on silica gel to provide the title compound (60%) as an oil, $R_f$=0.3 (20% ether/$CH_2Cl_2$).

Part B: 3α-ethylcarbonate-cis-5,10-bis-α,α-glucosyl cholic acid methyl ester

Palladium hydroxide (0.030 g, 15% by weight) is added to a mixture of the product of Part A (0.220 g, 0.014 mmol, 1.0 eq.) dissolved in benzene (4.0 ml) and methanol (32.0 ml) at room temperature. The mixture is hydrogenated at 50 psi for 48 hours. The product is filtered through Celite® (diatomaceous silica, Johns-Manville Corp.) under nitrogen. The solvent was evaporated and the oil was flash chromatographed with 0% methanol/methylene chloride. To remove the silica gel that dissolves under elution conditions, the product is run through on a reverse phase LH-20 column using methanol as an eluent. The solvent is evaporated to yield the title compound (65%) as a white powder, $R_f$=0.3 (15% MeOH/$CH_2Cl_2$), NMR ($CDCl_3$ 500 Mhz) δ:5.04 (m, Lh, anomeric β-H), 4.82 (m, Lh, anomeric β-H).

EXAMPLE 2

3α-benzoyl-cis-5,10-bis-β,β-glycosyl cholic acid methyl ester.

2,3,4,6-tetra-O-benzyl p-methoxy glucose sulfoxide (1.012 g, 1.45 mmol, 4.0 eq.), C3-O-benzoyl cholic acid methylester (0.191 g, 0.364 mmol, 1.0 eq.) and 2,6-di-tert-butyl-4 methyl pyridine (0,179 g, 0.874 mmol, 2.4 eq.) are azeotroped together three times from toluene (20 ml). After removing the toluene under reduced pressure for the last time, the mixture is dissolved in freshly distilled propionitrile and cooled under argon in a dry ice/acetone bath at −78° C. Triflic anhydride (244 μl, 1.45 mmol, 4.0 eq.) is added and the reaction mixture is stirred at −78° C. for 40 minutes. The reaction vessel is removed from the ice bath and stirred for an additional 10 minutes. The reaction is quenched by pouring it into saturated sodium bicarbonate and the product is isolated by extraction with methylene chloride and purified by flash chromatography on silica gel. Catalytic hydrogenation to remove the benzyl protecting groups is accomplished as described above to yield the title compound (60%) as an oil, $R_f$=0.3 (15% MeOH/$CH_2Cl_2$), NMR ($CDCl_3$ 500 Mhz) δ: 4.36 (d, 1H, J=7.92 Hz, anomeric α-H), 4.37 (d, 1H, J=7.92Hz, anomeric α-H).

The compounds of Example 1 and 2 and compounds which were prepared or could be prepared following procedures analogous to those outlined above are shown in Table I.

TABLE I

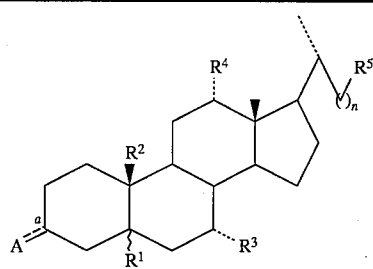

| EX | A | a* | $R^{1*}$ | $R^2$ | $R^{3}$ | $R^{4}$ | $R^5$ | n |
|---|---|---|---|---|---|---|---|---|
| 1[b] | O‖OCOEt | s(α) | H(β) | $CH_3$ | O-glucose(α) | O-glucose(α) | $CO_2Me$ | 2 |

TABLE I-continued

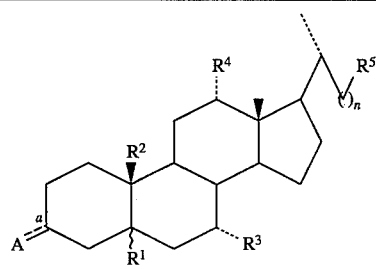

| EX | A | a* | R$^1$* | R$^2$ | R$^3$ | R$^4$ | R$^5$ | n |
|---|---|---|---|---|---|---|---|---|
| 2[c] | OCOPh | s(α) | H(β) | CH$_3$ | O-glucose(β) | O-glucose(β) | CO$_2$Me | 2 |
| 3[d] | OH | s(α) | H(β) | CH$_3$ | O-glucose(α) | O-glucose(α) | CO$_2$H | 2 |
| 4[e] | OH | s(α) | H(β) | CH$_3$ | O-glucose(α) | O-glucose(α) | CO$_2$Me | 2 |
| 5[f] | OH | s(α) | H(β) | CH$_3$ | O-glucose(α) | O-glucose(α) | CONH-Tryptophan | 2 |
| 6 | O=C(OEt) (OCOEt) | s(α) | H(α) | CH$_3$ | O-glucose(α) | O-glucose(α) | CO$_2$Me | 2 |
| 7[g] | OCOPh | s(α) | H(β) | CH$_3$ | O-glucose(α) | O-glucose(α) | CO$_2$Me | 2 |
| 8[h] | OCOPh—OMe | s(α) | H(β) | CH$_3$ | O-glucose(α) | O-glucose(α) | CO$_2$Me | 2 |
| 9[i] | OCOPh | s(α) | H(α) | CH$_3$ | O-glucose(β) | O-glucose(β) | CO$_2$Me | 2 |
| 10[j] | OH | s(α) | H(β) | CH$_3$ | O-glucose(β) | O-glucose(β) | CO$_2$H | 2 |
| 11[k] | OCOPh | s(α) | H(α) | CH$_3$ | O-glucose(α) | O-glucose(α) | CO$_2$Me | 2 |
| 12 | OH | s(α) | H(α) | CH$_3$ | O-glucose(α) | O-glucose(α) | CO$_2$H | 2 |
| 13[l] | OH | s(α) | H(α) | CH$_3$ | O-glucose(β) | O-glucose(β) | CO$_2$H | 2 |
| 14 | NH$_2$ | s(α) | H(β) | CH$_3$ | O-glucose(α) | O-glucose(α) | CO$_2$H | 2 |
| 15 | OCOEt | s(α) | H(β) | CH$_3$ | O-glucose(β) | O-glucose(β) | CO$_2$Me | 2 |
| 16 | OCOEt | s(α) | H(α) | CH$_3$ | O-glucose(β) | O-glucose(β) | CO$_2$Me | 2 |
| 17 | O | d | H(α) | CH$_3$ | O-glucose(α) | O-glucose(α) | CO$_2$H | 2 |
| 18 | O | d | H(α) | CH$_3$ | O-glucose(β) | O-glucose(β) | CO$_2$H | 2 |
| 19 | O | d | H(β) | CH$_3$ | O-glucose(α) | O-glucose(α) | CO$_2$H | 2 |
| 20 | O | d | H(β) | CH$_3$ | O-glucose(β) | O-glucose(β) | CO$_2$H | 2 |
| 21 | O | d | H(α) | CH$_3$ | O-glucose(α) | O-glucose(α) | CO$_2$Me | 2 |
| 22 | O | d | H(α) | CH$_3$ | O-glucose(β) | O-glucose(β) | CO$_2$Me | 2 |
| 23 | O | d | H(β) | CH$_3$ | O-glucose(α) | O-glucose(α) | CO$_2$Me | 2 |
| 24 | O | d | H(β) | CH$_3$ | O-glucose(β) | O-glucose(β) | CO$_2$Me | 2 |
| 25 | OCH$_2$Ph | s(α) | H(α) | CH$_3$ | O-glucose(α) | O-glucose(α) | CO$_2$H | 2 |
| 26 | OCH$_2$Ph | s(α) | H(α) | CH$_3$ | O-glucose(β) | O-glucose(β) | CO$_2$H | 2 |
| 27 | OCH$_2$Ph | s(α) | H(β) | CH$_3$ | O-glucose(α) | O-glucose(α) | CO$_2$H | 2 |
| 28 | OCH$_2$Ph | s(α) | H(β) | CH$_3$ | O-glucose(β) | O-glucose(β) | CO$_2$H | 2 |
| 29 | OCH$_2$Ph | s(α) | H(α) | CH$_3$ | O-glucose(α) | O-glucose(α) | CO$_2$Me | 2 |
| 30 | OCH$_3$Ph | s(α) | H(α) | CH$_3$ | O-glucose(β) | O-glucose(β) | CO$_2$Me | 2 |
| 31 | OCH$_2$Ph | s(α) | H(β) | CH$_3$ | O-glucose(α) | O-glucose(α) | CO$_2$Me | 2 |
| 32 | OCH$_2$Ph | s(α) | H(β) | CH$_3$ | O-glucose(β) | O-glucose(β) | CO$_2$Me | 2 |
| 33 | OCOEt | s(α) | H(α) | CH$_3$ | O-galactose(α) | O-galactose(α) | CO$_2$H | 2 |
| 34 | OCOEt | s(α) | H(α) | CH$_3$ | O-galactose(β) | O-galactose(β) | CO$_2$H | 2 |
| 35 | OCOEt | s(α) | H(β) | CH$_3$ | O-galactose(α) | O-galactose(α) | CO$_2$H | 2 |
| 36 | OCOEt | s(α) | H(β) | CH$_3$ | O-galactose(β) | O-galactose(β) | CO$_2$H | 2 |
| 37 | OCOEt | s(α) | H(α) | CH$_3$ | O-galactose(α) | O-galactose(α) | CO$_2$Me | 2 |

TABLE I-continued

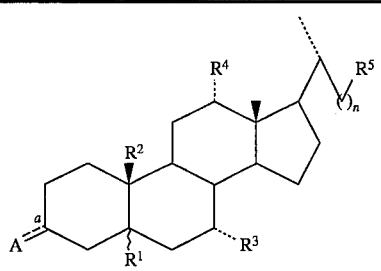

| EX | A | a* | R¹* | R² | R³ | R⁴ | R⁵ | n |
|----|---|----|----|----|------|------|----|---|
| 38 | O=COEt (OCOEt) | s(α) | H(α) | CH₃ | O-galactose(β) | O-galactose(β) | CO₂Me | 2 |
| 39 | OCOEt | s(α) | H(β) | CH₃ | O-galactose(α) | O-galactose(α) | CO₂Me | 2 |
| 40 | OCOEt | s(α) | H(β) | CH₃ | O-galactose(β) | O-galactose(β) | CO₂Me | 2 |
| 41 | OCOPh | s(α) | H(α) | CH₃ | O-ribose(α) | O-ribose(α) | CO₂H | 2 |
| 42 | OCOPh | s(α) | H(α) | CH₃ | O-ribose(β) | O-ribose(β) | CO₂H | 2 |
| 43 | OCOPh | s(α) | H(β) | CH₃ | O-ribose(α) | O-ribose(α) | CO₂H | 2 |
| 44 | OCOPh | s(α) | H(β) | CH₃ | O-ribose(β) | O-ribose(β) | CO₂H | 2 |
| 45 | OCOPh | s(α) | H(α) | CH₃ | O-ribose(α) | O-ribose(α) | CO₂Me | 2 |
| 46 | OCOPh | s(α) | H(α) | CH₃ | O-ribose(β) | O-ribose(β) | CO₂Me | 2 |
| 47 | OCOPh | s(α) | H(β) | CH₃ | O-ribose(α) | O-ribose(α) | CO₂Me | 2 |
| 48 | OCOPh | s(α) | H(β) | CH₃ | O-ribose(β) | O-ribose(β) | CO₂Me | 2 |
| 49 | OCOEt | s(α) | H(β) | CH₃ | O-glucose(α) | O-glucose(β) | CO₂Me | 2 |
| 50 | OCOEt | s(α) | H(β) | CH₃ | O-glucose(β) | O-glucose(α) | CO₂Me | 2 |
| 51 | OCOEt | s(α) | H(α) | CH₃ | O-glucose(α) | O-glucose(β) | CO₂Me | 2 |
| 52 | OCOEt | s(α) | H(α) | CH₃ | O-glucose(β) | O-glucose(α) | CO₂Me | 2 |

*s = single bond
d = double bond
α = below the plane of the ring
β = above the plane of the ring

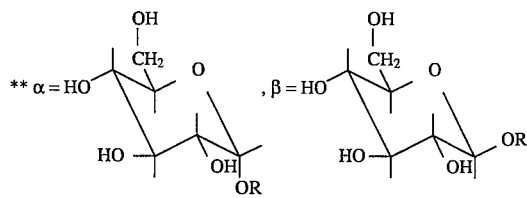

An α-glucoside    A β glucoside

Mass Spectra
c m/e = 851    l m/e = 771
d m/e = 771
h m/e = 881
i m/e = 851
j m/e = 771
k m/e = 851

¹H NMR
b: (CDCl₃, 500 MH$_z$) δ: 5.04(m, 1H, anomeric β-H), 4.82(m, 1H, anomeric β-H)
e: (CDCl₃, 500 MH$_z$) δ: 5.04(m, 1H, anomeric β-H), 4.82(m, 1H, anomeric β-H)
f: (CDCl₃, 500 MH$_z$) δ: 5.056(m, 1H, anomeric β-H), 5.0414(m, 1H, anomeric β-H)
g: (CDCl₃, 500 MH$_z$) δ: 5.0525(d, J=3.96H$_z$, 1H, anomeric β-H), 4.860(d, J=3.96Hz, 1H, anomeric β-H)

Use

The compounds of the invention have been shown to interact with, and permeabilize, biological membranes and to enhance the efficacy of antibiotics and antifungal agents on living cells. Since the compounds of the invention have been shown to permeabilize membranes, and the compounds themselves have no effect on cell growth at the concentrations used, it is assumed that the enhanced efficacy is related to increased delivery of the therapeutically-significant-compounds to the cells.

The utility of the compounds for permeabilizing membranes was demonstrated using an assay (Hoyt, D. W., et al. *Biochemistry*, Vol. 30, 10155 (1991)) in which a fluorescein derivative is encapsulated at self-quenching concentrations inside vesicles. An increase in fluorescent intensity upon addition of a test compound indicates leakage of the fluorescein derivative out of the vesicle and therefore implies a disruption of the membrane. The compounds of the present invention induced a rapid and significant increase in fluorescent intensity at very low concentrations (0.05 mM–0.5 mM), indicating phospholipid membrane permeabilization.

In addition, both light scattering and turbidity measurements on vesicles treated with selected glycosylated steroid derivatives (at concentrations which induce 100% leakage of carboxyfluorescein) showed that the average size of the vesicles was not significantly different from that of untreated vesicles. Moreover, electron micrographs of vesicles treated with selected glycosylated steroid derivatives (at concentrations which induce 100% leakage of carboxyfluorescein) did not show significant changes in morphology relative to untreated vesicles. The glycosylated steroid derivatives of the present invention, therefore, permeabilize membranes without destroying the vesicles or inducing extensive fusion.

The inventors believe, based on NMR studies of aggregation in solution and also on crystallographic evidence, that the glycosylated steroids of the present invention self-associate and insert into membranes in an associated form, and that membrane permeabilization is related to this process. Although the pure phospholipid vesicles used in this assay do not have the complexity of biological membranes, the inventors have shown that compounds which work well in this assay also enhance the action of therapeutically-significant-compounds (e.g., antibacterial agents and antifungal agents) on living cells. This finding supports the concept that the ability of the glycosylated steroid derivatives to interact with phospholipid bilayers is related to the ability of the derivatives to enhance therapeutic efficacy. It further indicates that the carboxyfluorescein assay is a reasonable initial model system for identifying potential candidates for the permeabilization of biological membranes.

A variation of the above assay (V. E. Carmichael et al. *J. Amer. Chem. Soc.*, Vol. III, 767 (1989)) was employed to determine whether the compounds make the membranes permeable to protons at extremely low concentrations (0.01 mM–0.005 mM). For this assay, the fluorescein derivative was encapsulated inside vesicles at non-quenching concentrations in a pH 6.5 buffer. The vesicles were diluted into a pH 5.5 buffer and a compound of Formula (I) was added at a concentration lower than the concentration required to make the membranes permeable to the fluorescein derivative. After addition of compounds of the Formula (I), the fluorescent intensity decreased, indicating that the membrane had become permeable to protons.

The utility of the glycosylated steroid derivatives of the invention for permeabilizing phospholipid membranes suggested the usefulness of the derivatives for enhancing the permeability of cell membranes, which are composed in large part of phospholipids and other lipids, to therapeutically-significant-molecules. This use was demonstrated in assays testing the efficacy of two different antifungal agents for killing *Crithidia fasciculata*. The use further was demonstrated in assays testing the efficacy of erythromycin for killing *E. Coli* ATCC 25922 cells.

Assay I: Leakage of Carboxyfluorescein from Vesicles

To a 25 mL round bottom flask 20.5 mg egg yolk (Sigma, average MW 770.4) dissolved in $CHCl_3$/MeOH, 5.0 mg phosphatidyl glycerol (Sigma, MW 772) dissolved in $CHCl_3$/MeOH, and 12.7 mg repurified cholesterol (Aldrich, MW 386.66) were added. The molar ratio of egg yolk; phosphatidyl glycerol:cholesterol was 4:1:5 (66 μmoles total lipid). The solvent was removed on a rotary evaporator. The dried lipid mixture was then put under argon and 3 mL freshly distilled diethyl ether was added. After the lipid had redissolved, 1 mL of carboxyfluorescein dissolved in water (pH adjusted to 7.4) was added to a concentration of 180 mM (the concentration of carboxyfluorescein was determined by UV; the extinction coefficient at pH 7.4 is $5.6 \times 10^4$; λmax=492). The lipid mixture containing carboxyfluorescein was sonicated under argon in a bath type sonicator at 5° –15° C. for 15–30 minutes. The mixture was then placed on the rotary evaporator and the organic solvent was removed. To separate the carboxyfluorescein-loaded vesicles from unencapsulated carboxyfluorescein, the remaining aqueous vesicle mixture was loaded on a Sephadex G-25 column equilibrated with 145 mM NaCl1/10 mM Hepes at pH 7.4. The carboxyfluorescein-loaded vesicles eluted in the first fraction after the void volume while the unencapsulated carboxyfluorescein remained on the column. The purified vesicles were diluted with 145 mM NaCl/10 mM Hepes buffer (pH 7.4) until the fluorescent intensity of the vesicle mixture measured approximately 10.

Because the carboxyfluorescein is encapsulated at self-quenching concentrations in the vesicles, an increase in fluorescent intensity over time indicates that the fluorophore is leaking out of the vesicles into the buffer. 5% Triton X100 was added in 50 μL MeOH to a sample of the vesicle solution to determine the maximum possible fluorescent increase (Triton X100 is a nonionic detergent that at the high concentration used breaks vesicles by solubilizing the lipids). The ability of each glycosylated steroid to induce the release of carboxyfluorescein from the vesicles was determined by monitoring the increase in fluorescent intensity upon addition of glycosteroid. For each experiment, 50 μL of glycosteroid in methanol (initial concentrations ranged from 0.6145 to 2.458 mM) was added to the cuvette and the fluorescent intensity followed over 10 minutes. A control in which 50 μL pure methanol was added showed that methanol alone does not cause a significant increase in fluorescent intensity. However, several of the glycosteroids efficiently permeabilized vesicle membranes at very low concentrations, permitting the carboxyfluorescein to leak out into the buffer. The results are summarized in Table II.

If the concentrations required to induce significant (i.e., >50%) leakage are taken as a measure of efficacy, then compounds 7, 8, and 11, are the most effective glycosylated steroids tested for permeabilizing phospholipid membranes in this assay. Compounds 7 and 8 have a cis A/B ring junction and two α-linked glucose sugars attached to the hydrophilic face of the molecule. Compound 11 also has two α-linked glucose sugars attached to the hydrophilic face of the molecule. Cholic acid, deoxycholic acid, and chenodeoxycholic acid, compounds known to permeabilize biological membranes in other uses (Gordon GS et al. *Proc. Nat'l. Acad. Sci.* USA 82:7419–7423 (1985)) also permeabilize membranes in this assay, although at much higher concentrations than many of the compounds of the present invention. From these observations, it may be concluded that glycosylation changes the chemical properties of the steroids, making them more efficient at permeabilizing membranes.

TABLE II

| EX | CONCENTRATION (mM)* | % increase in Fluorescence |
|---|---|---|
| Cholic Acid | 0.117 | 0 |
|  | 2.341 | 59.1 |
| Methyl Cholate | 0.117 | 25.4 |
| Chenodeoxycholic acid | 0.117 | 17.7 |
|  | 1.17 | 80.9 |
| Triton-X 100 | 4.04 | 100 |
|  | 1.17 | 46.4 |
|  | 0.117 | 18.6 |
| Deoxycholic Acid | 0.117 | 0 |
|  | 1.17 | 82.7 |
| 1 | 0.117 | 0 |
| 2 | 0.117 | 10 |
| 3 | 2.34 | 0 |
| 4 | 0.117 | 0 |
| 5 | 0.117 | 57.3 |
| 7 | 0.117 | 89.1 |
| 8 | 0.117 | 89.1 |
| 9 | 0.117 | 24.5 |
| 10 | 0.117 | 0 |
| 11 | 0.117 | 98 |
| 13 | 0.117 | 0 |

*Final concentration after dilution.

Assay II: Proton Transport Across Lipid Membranes

This assay was used to judge the ability of protons to pass across vesicle membranes treated with glycosteroids. Vesicles loaded with carboxyfluorescein at non-self-quenching concentrations were prepared exactly as described above except that the carboxyfluorescein was added to the lipid mixture in 1 mL water (pH 6.5) at a concentration of 1 mM. After sonication under argon and rotary evaporation to remove the diethyl ether, the carboxyfluorescein-loaded vesicles were purified on a Sephadex-G25 column as described above. The concentration of the vesicle solution after purification on the G-25 column was adjusted until the fluorescent intensity equaled 100 after 100-fold dilution into 80 mM NaCl/5 mM Hepes buffer at pH 5.5.

A 100-fold dilution of the vesicle stock into pH 5.5 buffer was made immediately before each experiment and 1 mL of the diluted solution was put in a cuvette. To evaluate the ability of the glycosteroids to facilitate transport of protons across the lipid bilayer, 50 μL of a 0.245M solution of each glycosteroid in methanol was added to the 1 mL vesicle solution in a fluorescence cuvette and the change in fluorescent intensity was monitored over a period of 10 minutes. A significant decrease in fluorescence indicates that the glycosteroid in question facilitates the transport of protons across the membrane. This assay is based on the fact that the fluorescent intensity of carboxyfluorescein is much greater at pH 6.5 than at pH 5.5. If vesicles prepared at pH 6.5 are diluted into a buffer at pH 5.5, the fluorescent intensity will drop over time as the pH gradient across the membrane collapses. As a control, 50 μL pure MeOH was added and the fluorescent intensity was found not to change significantly. Addition of MeOH at low concentrations therefore does not make the vesicles permeable to protons. The results are summarized in Table III.

TABLE III

| EX | Concentration (mM)* | % Decrease in Fluorescence |
|---|---|---|
| Triton-X 100 | 4.04 | 100 |
|  | 0.0116 | 2.43 |
| Gramicidin | 0.00579 | 87.2 |
|  | 0.000579 | 81.6 |
| Cholic Acid | 0.0116 | 1.0 |
| Methyl Cholate | 0.0116 | 5.4 |
| Chenodeoxycholic Acid | 0.0116 | 8.2 |
| Deoxycholic Acid | 0.0116 | 5.39 |
| 1 | 0.0116 | 7.6 |
|  | 0.00579 | 4.3 |
| 2 | 0.0116 | 8.6 |
|  | 0.00579 | 1.7 |
| 3 | 0.0116 | 35.4 |
|  | 0.00579 | 21.0 |
| 4 | 0.0116 | 12.3 |
|  | 0.00579 | 7.89 |
| 5 | 0.0116 | 26.1 |
|  | 0.00579 | 19.4 |
| 7 | 0.0116 | 19.8 |
|  | 0.00579 | 15.2 |
| 8 | 0.0116 | 32.2 |
|  | 0.00579 | 20.6 |
| 9 | 0.0116 | 43.0 |
|  | 0.00579 | 27.4 |
| 11 | 0.0116 | 22.0 |
|  | 0.00585 | 14.7 |
| 13 | 0.0116 | 70.6 |
|  | 0.00579 | 35.2 |
|  | 0.000579 | 2.8 |

*Final concentration after dilution.

ASSAY III: The Antibiotic Efficacy of Erythromycin With and Without Enhancers Erythromycin is an antibiotic whose efficacy is known to be increased by compounds that permeabilize cell membranes (Kubesch P. et al. *Biochemistry* 26: 2139–2149 (1987)). The efficacy of erythromycin, in the presence of novel glycosylated steroid derivatives of the present invention, was evaluated in a plate assay. Briefly, DH2 cells [a mutant strain of *E. coli* K-12, developed at Cold Spring Harbor Laboratories] grown in culture broth to an optical density [O.D.] of about 0.5 were mixed with 2.5 mL melted top agar [Top agar preparation: 10 grams tryptone (DIFCO), 5 grams yeast extract (DIFCO), 10 grams NaCl, 7 grams agar (DIFCO) and 1 mL 1M NaOH dissolved in one liter of pure water and autoclaved for 25 minutes] and then poured onto agar plates [agar plate preparation: 10 grams tryptone, 5 grams yeast, 10 grams NaCl1, 15 grams agar, and 1 mL 1M NaOH dissolved in one liter pure water, autoclaved and cooled]. After cooling for 15–30 minutes, each plate was divided into a grid and 4 μl of a test solution containing erythromycin [0.5 mM or 1.0 mM] in methanol, or erythromycin plus test compound [20 mM] in methanol, was spotted on each section of the grid. The plates were incubated for sixteen (16) hours at 37 ° C. and then examined for zones of inhibition (i.e., clear areas in sections of the grid where the test solution inhibited bacterial cell growth). Each section of the grid was scored. The section of the grid containing erythromycin alone at 1.0 mM concentration was used as a standard for evaluating efficacy, with the other sections scored. relative to this. The results, summarized in Table IV below show that 3α-O-p-methoxybenzoyl-cis-5, 10-bis-α,α-7,12-glucosyl cholic acid methyl ester [hereinafter referred to as "CME"] is the best enhancer in this assay. Of the non-glycosylated, bile acid derivatives used in this assay, only deoxycholic acid and its sodium salt showed any effect. Chenodeoxycholic acid and cholic acid and its salts did not have a detectable effect on the antibiotic efficacy of erythromycin in this assay. Interestingly, deoxycholic acid salts also have been shown to be more effective than chenodeoxycholic acid salts and cholic acid salts in enhancing the uptake of insulin through nasal membranes (Gordon GS et al. *Proc. Nat'l. Acad. Sci.* USA, 82:7419–7423 (1985)).

TABLE IV

| COMPOUND (20 mM) | ERYTHROMYCIN (mM) | EFFECT |
| --- | --- | --- |
| Cholic Acid | 1.0 mM | − |
| Cholic Acid | 0.5 mM | − |
| Sodium Cholate | 1.0 mM | − |
| Sodium Cholate | 0.5 mM | − |
| Methyl Cholate | 1.0 mM | − |
| Methyl Cholate | 0.5 mM | − |
| Chenodeoxycholic Acid | 1.0 mM | − |
| Chenodeoxycholic Acid | 0.5 mM | − |
| Deoxycholic Acid | 1.0 mM | + |
| Deoxycholic Acid | 0.5 mM | + |
| Sodium Deoxycholate | 1.0 mM | + |
| Sodium Deoxycholate | 0.5 mM | + |
| CME | 1.0 mM | +++ |
| CME | 0.5 mM | +++ |
| 3α-O-benzoyl-trans-5,10-bis-α,α-7,12-glucosyl cholic acid methyl ester [BTME] | 1.0 mM | + |
| BTME | 0.5 mM | + |
| 3α-OH-cis-5,10-bis-α,α glucosyl cholic acid K⁺ | 1.0 mM | + |
| 3α-OH-cis-5,10-bis-α,α glucosyl cholic acid K⁺ | 0.5 mM | + |

−: erythromycin alone at 1.0 mM (baseline) and all lesser effects
+: enhancement relative to baseline
+++: significant enhancement relative to baseline The above plate assay was repeated using lower concentrations of CME and comparing its efficacy as an enhancer to that of the non-glycosylated parent, 3α-O-p-methoxybenzoyl-cis-5,10-cholic acid methyl ester [hereinafter referred to as "CDE"]. The results, summarized in Table V below, show that while CME acts as an enhancer at very low concentrations, the non-glycosylated parent compound does not function as an enhancer. This demonstrates that the sugars are critical for enhancing effect.

TABLE V

| COMPOUND (mM) | ERYTHROMYCIN (mM) | EFFECT |
| --- | --- | --- |
| 1.0 mM CDE | 0.1 mM | − |
| 0.1 mM CDE | 0.1 mM | − |
| 0.1 mM CME | 0.1 mM | + |
| 0.1 mM CME | 0.01 mM | + |
| 0.01 mM CME | 0.01 mM | + |
| 0.001 mM CME | 0.01 mM | + |
| 0.001 mM CME | 0.001 mM | − |

−: no detectable clearing (zone of inhibition)
+: visible clearing

Assay IV: Efficacy of Antifungal Agents on Protozoa With and Without Added Glycosylated Steroid Derivatives CME, identified in both Assay I described above (compound 8 in the carboxyfluorescein assay) and in Assays II and III described above, as a good membrane permeabilizing agent, was tested for its ability to enhance the efficacy of two different antifungal agents on the protozoan *Crithidia fasciculata*. The ability of the non-glycosylated parent steroid to enhance efficacy was also studied. The studies were carried out as described in Pascal RA et al. *Biochemistry* 22: 171–178 (1983) and Rahman MD et al. *J. Med. Chem.* 31:1656–1659 (1988). Briefly, flasks containing 25 mL of growth medium [Preparation: 1.5 grams sucrose, 0.5 grams yeast extract, 0.4 grams tryptone and 0.25 mL triethanolamine dissolved in 100 mL water and pH adjusted to 8.0 with 10M HCl. Autoclave. After cooling, add 100 µL hemin (SIGMA) (2 mg hemin/1 mL 0.1N NaOH) and 20 mg. streptomycin sulfate (SIGMA)] and the antifungal agent and/or the glycosylated or non-glycosylated steroid derivatives were inoculated with aliquots of *C. fasciculata* (250 µL of culture containing approximately $1\times10^6 - 1 \times 10^7$ cells) [Preparation of culture: *C. fasciculata* in glycerol added to culture medium and grown, with shaking, for three (3) days at 26° C.; then stored at 0° to 4° C.]. The cultures were incubated, with shaking, at 25° C. and growth was monitored by changes in absorbance at 535 nm (relative to the uninoculated medium).

Figure 2:
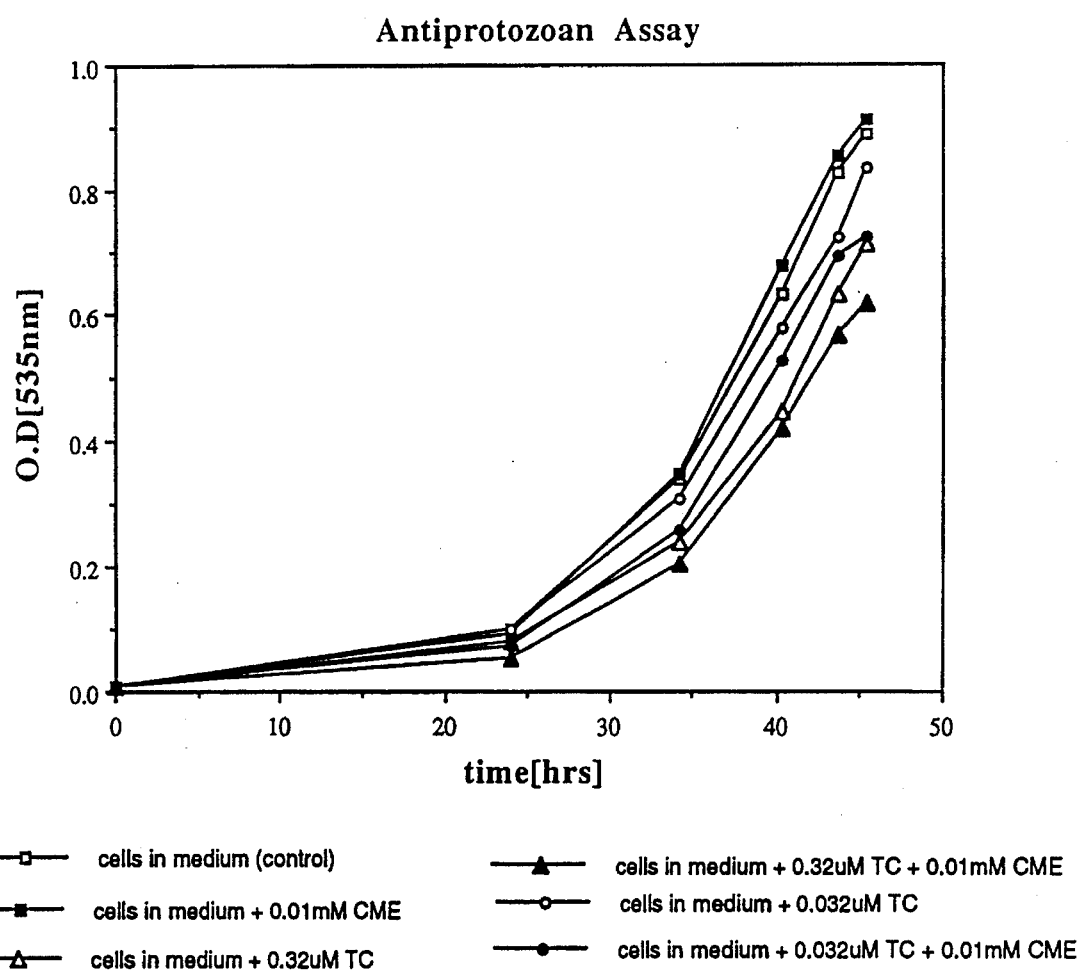
FIG. 2. A graph depicting the enhancing effect of CME, a novel glycosylated steroid derivative of the present invention, on the efficacy of thiacholestanol, an antifungal agent.
Figure 3:
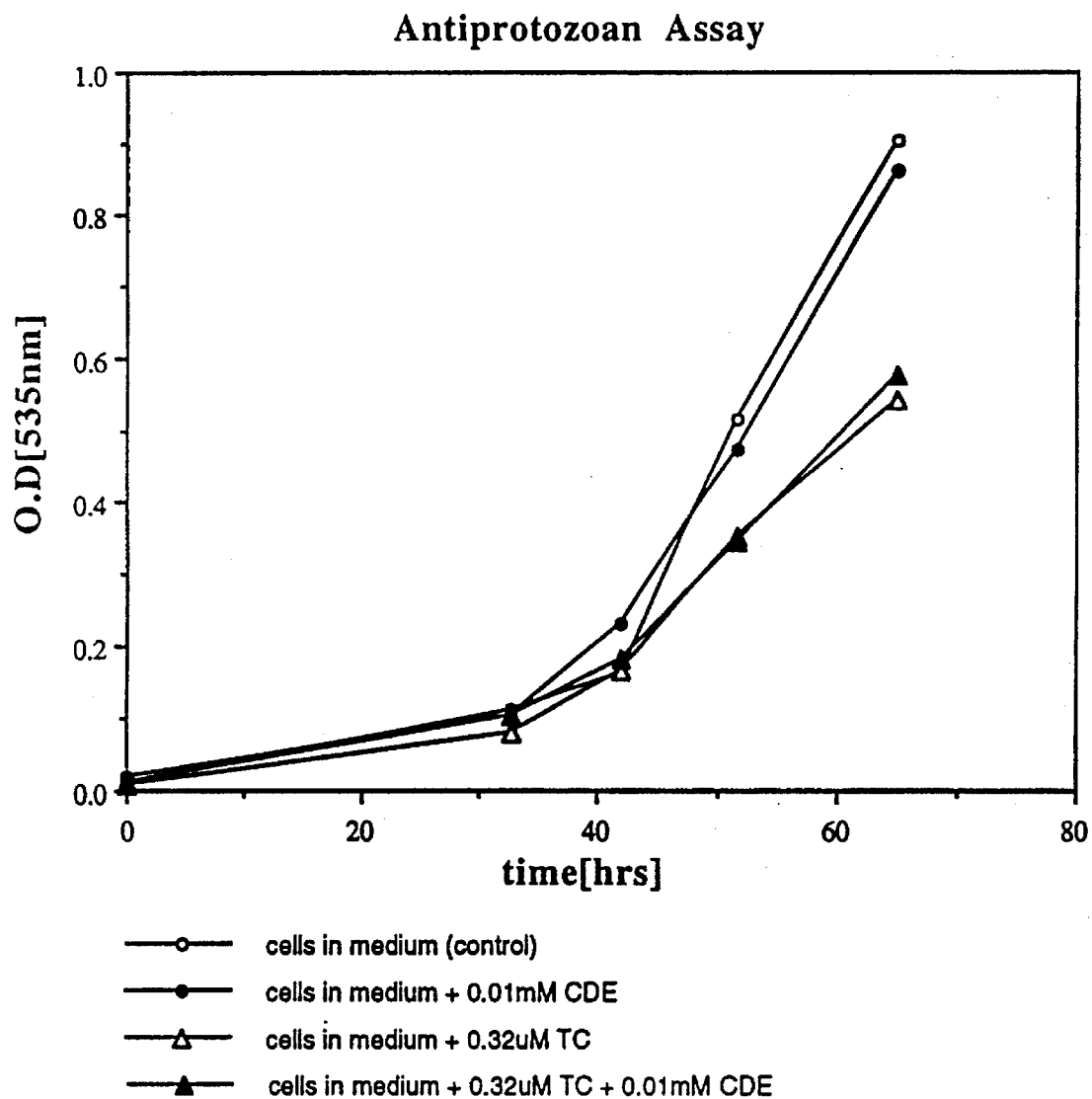
FIG. 3. A graph depicting the lack of an enhancing effect of CDE, the non-glycosylated version of CME, on the efficacy of thiacholestanol, an antifungal agent.

Two different antifungal agents were used in the assays. The first was 10-thiastearic acid (10-TSA; see Rahman MD et al. *J. Med. Chem.* 3:1656–1659), which has an $IC_{50}$ of 10 µM; the second was 24-thiacholestanol (24-TC; see Rahman MD et al. *J. Lipid Research* 29:1543–1548 (1988); Rahman MD and Pascal RA. *J. Biol. Chem.* 265:4989–4996 (1990)), which has an $IC_{50}$ of 0.32 µM. The results, depicted in FIGS. 1, 2, and 3, demonstrate that the presence of CME enhances the efficacy of 10-TSA dramatically, allowing it to be used in 10- to 100-fold lower concentrations than otherwise necessary to achieve 50% inhibition of growth [FIG. 1]. The presence of CME also was shown to enhance the efficacy of 24-TC [FIG. 2]. The non-glycosylated parent steroid (CDE) was not observed to act as an enhancer in this assay [FIG. 3].

Assay V: Efficacy of Derivative-Compound-Conjugate on the Protozoa *Crithidia Fasciculata*

A novel glycosylated steroid derivative of Formula (1) is conjugated to a therapeutically-significant-compound by methods known in the art for coupling an acid group to an amine. The ability of the derivative-compound-conjugate to inhibit the growth of *Crithidia fasciculata* is evaluated as described in Pascal RA et al. *Biochemistry* 22:171–178 (1983) and Rahman MD et al. *J. Med. Chem.* 31: 1656–1659 (1988). Briefly, flasks containing 25 mL growth medium alone, growth medium plus 24-TC at 0.32 µM concentration (the $IC_{50}$ level), and growth medium plus the derivative-compound-conjugate at 0.32 µM concentration are inoculated with aliquots of *C. fasciculata* (250 µL of culture containing approximately $1\times10^6 - 1\times10_7$ cells). The cultures are incubated with shaking at 25° C. and growth is monitored by changes in absorbance at 535 nm (relative to the uninoculated medium). Enhanced efficacy of the derivative-compound-conjugate relative to the non-conjugated therapeutically-significant-compound would be reflected in a lower rate of growth (i.e., lower absorbance over time). The $IC_{50}$ level of the derivative-compound-conjugate can be measured by repeating the experiments with different concentrations of derivative-compound-conjugate to define the concentration which causes a 50% inhibition of growth relative to the culture containing *C. fasciculata* alone.

In another set of experiments, the flasks of growth medium contain derivative-compound-conjugate at its $IC_{50}$ value, as defined in the above experiments, plus a glycosylated steroid of the present invention, such as CME, which is known to increase the efficacy of 24-TC when not conjugated [hereinafter referred to as "the enhancer"]. The enhancer is present at the following ratios relative to the derivative-compound-conjugate: 0:1, 0.1:1, 1:1, 10:1, 100:1, 1000:1, or any concentration in between. The medium is inoculated with aliquots of *C. fasciculata* as described above and growth is monitored by changes in the absorbance at 535 nm relative to the uninoculated medium. Increased efficacy of the derivative-compound-conjugate in the presence of the enhancer is reflected in a lower rate of growth relative to the derivative-compound-conjugate alone. The optimum ratio of enhancer:derivative-compound-conjugate is defined as that ratio which gives the lowest rate of growth.

What is claimed is:

1. A compound-conjugate comprising a compound of the formula (I) conjugated through any of A, C-3, or $R^5$ to a therapeutically-significant-compound:

(I)

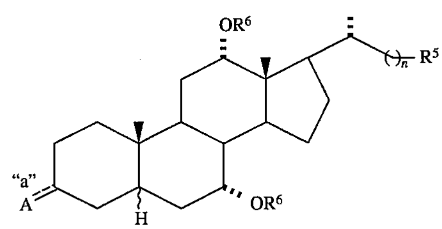

wherein

A is O, OH, $OR^6$, $NR^7R^8$, $N_3$, $NHCOR^7$, OCOAr, O-CO-$OR^9$, $OCOR^9$, $NHCH_2C_6H_5$, and in which Ar is phenyl or phenyl substituted with 1–3 groups selected from the group consisting of halogen, $C_1$–$C_{12}$ alkyl or $C_1$–$C_3$ alkoxy;

"a" is a single bond in the alpha or beta configuration with the proviso that when A =O, "a" is a double bond;

$R^5$ is $CO_2R^{10}$, $CH_2OR^9$, $CONH_2$, $CONHR^7$, $CONR^7R^8$, CO-S-$R^{10}$, $CH^2S(O)_p$-S-$R^{10}$, $CH_2NH_2$, $CH_2NHR^7$, $CH_2NR^7R^8$, $CH_2$-$SO(O)_p$-S-$R^{10}$;

$R^6$ is a glycosyl moiety comprising 1–10 monosaccharide units in which the glycosidic linkage at the anomeric carbon of each monosaccharide unit is independently alpha or beta;

$R^7$ and $R^8$, independently are H, $C_1$–$C_4$ alkyl, $C_3$–$C_7$ cycloakyl, $C_4$–$C_{10}$ alkylcycloalkyl, phenyl, benzyl, or, taken together are $(CH_2)_f$, where f=3–6;

$R^9$ is H, or $C_1$–$C_3$ alkyl;

$R^{10}$ is H, $C_1$–$C_{10}$ alkyl, $C_1$–$C_{10}$ alkenyl, $C_1$–$C_{10}$ alkynyl, $C_6H_5$ or $CH_2C_6H_5$;

p is 0, 1 or 2;

n is 0, 1 or 2;

or a pharmaceutically suitable salt thereof.

2. The compound-conjugate of claim 1 conjugated to a therapeutically-significant compound, in which A is OH, $OR^6$, O—CO—$OR^9$, $OCOC_6H_5$, $OCOC_6H_5$-pOMe, $NH_2$;

"a" is a single bond;

$R^5$ is $CO_2R^{10}$, $CONR^7R^8$;

$R^6$ is a glycosyl moiety comprising a protected or deprotected hexose or deoxy derivative thereof having an anomeric alpha or beta glycosidic linkage; and $R^{10}$ is H or $C_1$–$C_{10}$ alkyl.

3. The compound-conjugate of claim 1 comprising 3α-O-p-methoxybenzoyl-cis-5,10-bis-α,α-7,12-glucosyl cholic acid methyl ester conjugated to a therapeutically-significant-compound.

4. The compound-conjugate of claim 1 comprising 3α-O-p-methoxybenzoyl-cis-5,10-bis-α,α-7,12-glucosyl cholic acid conjugated to a therapeutically-significant-compound.

5. The compound-conjugate of claim 4 wherein the therapeutically-significant-compound is an antifungal agent.

6. The compound-conjugate of claim 5 wherein the antifungal agent is 24 thiacholestanol.

7. A pharmaceutical composition comprising an effective amount of a compound-conjugate of claim 1 and a suitable pharmaceutical carrier.

8. A pharmaceutical composition comprising an effective amount of a compound-conjugate of claim 2 and a suitable pharmaceutical carrier.

9. A pharmaceutical composition comprising an effective amount of a compound-conjugate of claim 3 and a suitable pharmaceutical carrier.

10. A pharmaceutical composition comprising an effective amount of a compound-conjugate of claim 4 and a suitable pharmaceutical carrier.

11. A pharmaceutical composition comprising an effective amount of a compound-conjugate of claim 1, the compound of the formula (I), and a suitable pharmaceutical carrier.

12. A pharmaceutical composition comprising an effective amount of a compound-conjugate of claim 2 a compound of the formula (I), and a suitable pharmaceutical carrier.

13. A pharmaceutical composition comprising an effective amount of a compound-conjugate of claim 3, a compound of the formula (I), and a suitable pharmaceutical carrier.

14. A pharmaceutical composition comprising an effective amount of a compound-conjugate of claim 4, a compound of the formula (I), and a suitable pharmaceutical carrier.

15. The pharmaceutical composition of claim 7 in which A is OH, $OR^6$, O—CO—$OR^9$, $OCOC_6H_5$, $OCOC_6H_5$—pOMe or $NH_2$.

16. The pharmaceutical composition of claim 7 in which A is $NH_2$.

17. The pharmaceutical composition of claim 7 in which "a" is a single bond.

18. The pharmaceutical composition of claim 7 in which $R^5$ is $CO_2R^{10}$ or $CONR^7R^8$.

19. The pharmaceutical composition of claim 7 in which $R^6$ is a glycosyl moiety comprising a monosaccharide or deoxymonosaccharide thereof having an anomeric alpha (α) glycosidic linkage.

20. The pharmaceutical composition of claim 7 in which $R^6$ is a glycosyl moiety comprising a monosaccharide or a deoxymonosaccharide thereof having an anomeric beta (β) glycosidic linkage.

21. The pharmaceutical composition of claim 7 in which $R^{10}$ is H or $C_1$–$C_{10}$ alkyl.

22. The pharmaceutical composition of claim 19 which said monosaccharide is 2,3,4,6-Tetra-O-benzyl D-glucose.

23. The pharmaceutical composition of claim 20 in which said monosaccharide is 2,3,4,6-Tetra-O-benzyl D-glucose.

24. The pharmaceutical composition of claim 19 in which said monosaccharide is D-glucose.

25. The pharmaceutical composition of claim 20 in which said monosaccharide is D-glucose.

26. The pharmaceutical composition of claim 7 in which said compound of formula (I) is 3α-O-Benzoyl-trans-5,10-bis-β,β-7,12-glucosyl cholic acid methyl ester.

27. The pharmaceutical composition of claim 7 in which said compound of formula (I) is 3α-Hydroxy-cis-5,10-bis-α,α-7,12-glucosyl cholic acid.

28. The pharmaceutical composition of claim 7 in which said compound of formula (I) is 3α-Hydroxy-cis-5,10-bis-α,α-7,12-glucosyl cholic acid methyl ester.

29. The pharmaceutical composition of claim 7 in which said compound of formula (I) is 3α-Hydroxy-cis-5,10-bis-α,α-7,12-glucosyl-25-tryptophanyl cholic acid.

30. The pharmaceutical composition of claim 7 in which said compound of formula (I) is 3α-ethylcarbonate-cis-5,10-bis-α,α-7,12-glucosyl cholic acid methyl ester.

31. The pharmaceutical composition of claim 7 in which said compound of formula (I) is 3α-O-Benzoyl-cis-5,10-bis-α,α-7,12-glucosyl cholic acid methyl ester.

32. The pharmaceutical composition of claim 7 in which said compound of formula (I) is 3α-O-Benzoyl-cis-5,10-bis-β,β-7,12-glucosyl cholic acid methyl ester.

33. The pharmaceutical composition of claim 7 in which said compound of formula (I) is 3α-Hydroxy-cis-5,10-bis-β,β-7,12-glucosyl cholic acid.

34. The pharmaceutical composition of claim 7 in which said compound of formula (I) is 3α-O-Benzoyl-trans-5,10-bis-α,α-7,12-glucosyl cholic acid methyl ester.

35. The pharmaceutical composition of claim 7 in which said compound of formula (I) is 3α-Hydroxy-trans-5,10-bis-β,β-7,12-glucosyl cholic acid.

36. The pharmaceutical composition of claim 7 in which said compound of formula (I) is 3α-O-p-Methoxybenzoyl-cis5,10,-bis-α,α-7,12-glucosyl cholic acid methyl ester.

37. The compound-conjugate of claim 1 wherein the compound of formula (I) is conjugated to the therapeutically-significant-compound through any of $R_5$.

38. The compound-conjugate of claim 1 wherein the compound of formula (I) is conjugated to the therapeutically-significant-compound through an amide functionality.

39. The compound-conjugate of claim 1 wherein the therapeutically-significant-compound is a peptide.

40. The compound-conjugate of claim 38 wherein the therapeutically-significant-compound is a peptide.

41. The compound-conjugate of claim 1 wherein the therapeutically-significant-compound is a nucleotide.

42. The compound-conjugate of claim 38 wherein the therapeutically-significant-compound is a nucleotide.

43. The compound-conjugate of claim 1 wherein the compound of formula (I) is conjugated to the therapeutically-significant-compound through an amine functionality.

44. The compound-conjugate of claim 1 wherein the compound of formula (I) is conjugated to the therapeutically-significant-compound through an ether functionality.

45. The compound-conjugate of claim 1 wherein the compound of formula (I) is conjugated to the therapeutically-significant-compound through an ester functionality.

46. The compound-conjugate of claim 1, wherein the therapeutically-significant-compound is an antifungal agent.

47. The compound-conjugate of claim 38, wherein the therapeutically-significant-compound is an antifungal agent.

48. The compound-conjugate of claim 1 in which A is OH, $OR^6$, O—CO—$OR^9$, $OCOC_6H_5$, $OCOC_6H_4$—pOMe or $NH_2$.

49. The compound-conjugate of claim 1 in which "a" is a single bond.

50. The compound-conjugate of claim 1 in which said glycosyl moiety is a hexose selected from the group consisting of D-allose, D-altrose, D-glucose, D-mannose, D-gulose, D-idose, D-galactose, D-talose or a deoxyhexose.

51. The compound-conjugate of claim 1 in which said glycosyl moiety is a furanose selected from the group consisting of D-ribose, D-arabinose, D-xylose, D-lyxose or a deoxyfuranose.

52. The compound-conjugate of claim 1 in which $R^6$ comprises a monosaccharide in which the glycosidic linkage at the anomeric carbon of said monosaccharide is alpha (α).

53. The compound-conjugate of claim 1 in which $R^6$ comprises a monosaccharide in which the glycosidic linkage at the anomeric carbon of said monosaccharide is beta (β).

54. The compound-conjugate of claim 52 in which said monosaccharide is 2,3,4,6-tetra-O-benzyl-D-glucose.

55. The compound-conjugate of claim 53 in which said monosaccharide is 2,3,4,6-tetra-O-benzyl-D-glucose.

56. The compound-conjugate of claim 52 in which said monosaccharide is D-glucose.

57. The compound-conjugate of claim 53 in which said monosaccharide is D-glucose.

58. The compound-conjugate of claim 1 in which the compound of the formula (I) is 3α-hydroxy-cis-5,10-bis-α,α-7,12-glucosyl cholic acid.

59. The compound-conjugate of claim 1 in which the compound of the formula (I) is 3α-hydroxy-cis-5,10-bis-α,α-7,12-glucosyl-25-tryptophanyl cholic acid.

60. The compound-conjugate of claim 1 in which the compound of the formula (I) is 3α-hydroxy-cis-5,10-bis-β,β-7,12-glucosyl cholic acid.

61. The compound-conjugate of claim 1 in which the compound of the formula (I) is 3α-hydroxy-trans5,10-bis-β,β-7,12glucosyl cholic acid.

62. The compound-conjugate of claim 50 in which said hexose or deoxyhexose thereof is protected with a protecting group selected from the group consisting of benzyl, pivaloyl, trimethylsilyl, tert-butyldimethylsilyl, tertbutyldiphenylsilyl, tri-isopropylsilyl, acetyl, tetrahydropyranyl, benzoyl, $C_1$–$C_3$ alkyl, isopropylidene, benzylidene, (2-methoxyethoxy) methyl, orthoester, paramethoxybenzyl or allyl.

63. The compound-conjugate of claim 51 in which said furanose or deoxyfuranose derivative thereof is protected with a protecting group selected from the group consisting of benzyl, pivaloyl, trimethylsilyl, tert-butyldimethylsilyl, tertbutyldiphenylsilyl, tri-isopropylsilyl, acetyl, tetrahydropyranyl, benzoyl, $C_1$–$C_3$ alkyl, isopropylidene, benzylidene, (2-methoxyethoxy)methyl, orthoester, paramethoxybenzyl or allyl.

64. The pharmaceutical composition of claim 7 which is in the form of a powder, capsule, or tablet.

65. The pharmaceutical composition of claim 7 which is injectable.

66. The pharmaceutical composition of claim 7 which is in the form of a suspension.

67. The pharmaceutical composition of claim 7 which is in the form of a nasal spray or lung inhaler.

68. The pharmaceutical composition of claim 7 which is in the form of a topical formulation.

\* \* \* \* \*